United States Patent
Seok et al.

(10) Patent No.: US 9,437,825 B2
(45) Date of Patent: Sep. 6, 2016

(54) HOLE-TRANSPORTING MATERIAL FOR INORGANIC/ORGANIC HYBRID PEROVSKITE SOLAR CELLS

(71) Applicant: KOREA RESEARCH INSTITUTE OF CHEMICAL TECHNOLOGY, Daejeon (KR)

(72) Inventors: Sang Il Seok, Daejeon (KR); Jaemin Lee, Daejeon (KR); Hak Guen Lee, Busan (KR); Nam Joong Jeon, Gwangju (KR); Jangwon Seo, Seoul (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 14/696,966

(22) Filed: Apr. 27, 2015

(65) Prior Publication Data
US 2015/0311440 A1     Oct. 29, 2015

(30) Foreign Application Priority Data

Apr. 28, 2014 (KR) .................. 10-2014-0050995
Apr. 24, 2015 (KR) .................. 10-2015-0057688

(51) Int. Cl.
*H01L 51/00* (2006.01)
*C07C 217/84* (2006.01)
*H01L 51/42* (2006.01)

(52) U.S. Cl.
CPC .......... *H01L 51/006* (2013.01); *C07C 217/84* (2013.01); *C07C 2103/94* (2013.01); *H01L 51/4226* (2013.01); *Y02E 10/549* (2013.01)

(58) Field of Classification Search
CPC .................................................. H01L 51/5056
See application file for complete search history.

(56) References Cited

U.S. PATENT DOCUMENTS

2013/0199603 A1*   8/2013   Snaith .................. H01L 51/422
                                                             136/255

FOREIGN PATENT DOCUMENTS

KR          10-1172534 B1      8/2012

OTHER PUBLICATIONS

Julian Burschka, et al; "Sequential deposition as a route to high-performance perovskite-sensitized solar cells", Nature, vol. 499, Jul. 18, 2013, pp. 316-320.

* cited by examiner

*Primary Examiner* — Devina Pillay
*Assistant Examiner* — Daniel Malley, Jr.
(74) *Attorney, Agent, or Firm* — Ladas & Parry LLP

(57) ABSTRACT

Provided is a hole-transporting compound having a novel structure, and more particularly, a hole-transporting compound for an inorganic/organic hybrid perovskite solar cell. An inorganic/organic hybrid perovskite-based solar cell using the hole-transporting compound according to the present invention has significantly high power generation efficiency.

9 Claims, 1 Drawing Sheet

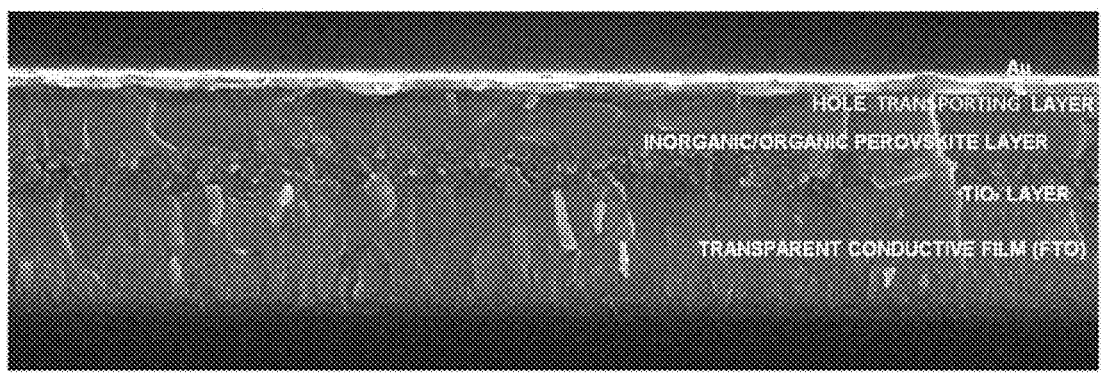

HOLE-TRANSPORTING MATERIAL FOR INORGANIC/ORGANIC HYBRID PEROVSKITE SOLAR CELLS

CROSS-REFERENCE TO RELATED APPLICATIONS

This application claims priority under 35 U.S.C. §119 to Korean Patent Application No. 10-2014-0050995 filed on Apr. 28, 2014 and Korean Patent Application No. 10-2015-0057688 filed on Apr. 24, 2015 in the Korean Intellectual Property Office, the disclosure of which is incorporated herein by reference in its entirety.

TECHNICAL FIELD

The following disclosure relates to a hole-transporting compound, and more particularly, to a hole-transporting compound having a novel structure, capable of being used in an inorganic/organic hybrid perovskite solar cell.

BACKGROUND

In order to solve depletion of fossil energy and earth-environmental problems caused by using fossil energy, research into alternative clean energy sources such as solar energy, wind energy, and hydro energy that are recyclable and clean has been actively conducted.

Among them, an interest in a solar cell directly converting solar lights into electric energy has significantly increased. Here, the solar cell means a cell generating current-voltage using a photovoltaic effect that the cell absorbs light energy from the solar lights to generate electrons and holes.

Currently, an n-p diode type single-crystalline silicon (Si) based solar cell having photovoltaic conversion efficiency higher than 20% may be manufactured and actually used in solar power generation, and there is a solar cell using a compound semiconductor such as gallium arsenide (GaAs) having conversion efficiency higher than that of the n-p diode type single-crystalline silicon (Si) based solar cell. However, since these inorganic semiconductor based solar cells require a very highly purified material for high efficiency, a large amount of energy is consumed in purifying a raw material, and expensive processing equipment is required during a single crystallization process or a thinning process using the raw material, such that there is a limitation in lowering manufacturing cost of the solar cell, thereby blocking large-scale use of the solar cell.

Therefore, in order to manufacture the solar cell at low cost, cost of a core material used in the solar cell or the manufacturing process of the solar cell should be greatly reduced, and research into a dye-sensitized solar cell (DSSC) and an organic photovoltaic that may be manufactured using an inexpensive material and process has been actively conducted as an alternative to the inorganic semiconductor based solar cell.

The dye-sensitized solar cell (DSSC) was initially developed by Michael Gratzel in 1991, a professor at EPFL in Switzerland and was reported in Nature.

An early dye-sensitized solar cell had a simple structure in which a dye absorbing light was adsorbed on porous photoanodes on a transparent electrode film through which light and electricity flow, another conductive glass substrate was positioned on the film, and a liquid electrolyte was filled therebetween.

An operation principle of the dye-sensitized solar cell is as follows. When dye molecules chemically adsorbed on surfaces of the porous photoanodes absorb solar light, the dye molecules generate electron-hole pairs, and electrons are injected into a conduction band of semiconducting oxides used as the porous photoanodes to be transported to the transparent conductive film, thereby generating current. The holes remaining in the dye molecules configure a complete solar cell circuit in a form in which the holes are transported to photocathodes by hole conduction due to an oxidation-reduction reaction of a liquid or solid electrolyte or a hole-conductive polymer, thereby performing external work.

Meanwhile, the organic photovoltaic (OPV) is configured of organic materials having electron donor (D, or often called a hole acceptor) characteristics and electron acceptor (A) characteristics. When the solar cell made of organic molecules absorbs light, electrons and holes are formed, which are called exciton. The exciton moves to a D-A interface, such that an electric charge is separated, an electron moves to the electron acceptor, and the hole moves to the electron donor, thereby generating photo current.

Since a distance at which the exciton generated in the electron donor may move is about 10 nm, which is significantly short, photo active organic materials may not be thickly laminated, such that optical absorbance was low and the efficiency was low. However, recently, due to introduction of a so-called bulk heterojunction (BHJ) concept of increasing a surface area at an interface and development of an electron donor organic material having a small band gap to easily absorb solar lights in a wide range, the efficiency was significantly increased, such that an organic photovoltaic having efficiency higher than about 10% has been reported.

In the organic photovoltaic, a manufacturing process of a device is simple as compared to the existing solar cell due to high formability of the organic material, diversity thereof, and low cost thereof, such that the organic photovoltaic may be manufactured at low cost, as compared to the existing solar cell. However, the organic photovoltaic has a problem in that a structure of the BHJ is degraded by moisture in air or oxygen, which rapidly decreases the efficiency of the solar cell, that is, a problem in the stability of the solar cell. When a technology of completely sealing the solar cell is introduced in order to solve this problem, the stability may be increased, but the cost may also be increased.

As a method of solving problems of the DSSC by the liquid electrolyte, an all-solid state DSSC using Spiro-OMeTAD[2,2',7,7'-tetrkis (N,N-di-p-methoxyphenylamine)-9,9'-spirobi fluorine], which is a solid state hole conductive organic material, rather than the liquid electrolyte to thereby have efficiency of 0.74% was reported in Nature in 1998 by Michael Gratzel, a chemistry professor at EPFL in Switzerland, who is an inventor of the DSSC.

Therefore, research into a technology of applying the spiro-OMeTAD, which is a hole conductive material, to a perovskite solar cell to achieve high efficiency was conducted (J. Burschka, N. Pellet, S. J. Moon, R. Humphry-Baker, P. Gao, M. K. Nazeeruddin and M. Gratzel, Nature, 2013, 499, 316-319).

However, a solar cell having high efficiency capable of being commercialized has been still required.

RELATED ART DOCUMENT

Patent Document (Patent Document 1) Korean Patent No. 1172534

Non-Patent Document (Non-Patent Document 1) Nature, 2013, 499, 316-319

SUMMARY

An embodiment of the present invention is directed to providing a hole-transporting compound having a novel structure, capable of being used in a high efficiency inorganic/organic hybrid perovskite solar cell.

In one general aspect, a hole-transporting compound for an inorganic/organic hybrid perovskite solar cell having a novel structure, capable of being used in an inorganic/organic hybrid perovskite solar cell, being easily synthesized and separated, and improving efficiency by effectively blocking electrons released from the inorganic/organic hybrid perovskite due to a high lowest unoccupied molecular orbital (LUMO) level as compared to an existing single molecule hole-transporting compound, the hole-transporting compound is represented by Chemical Formula 1.

[Chemical Formula 1]

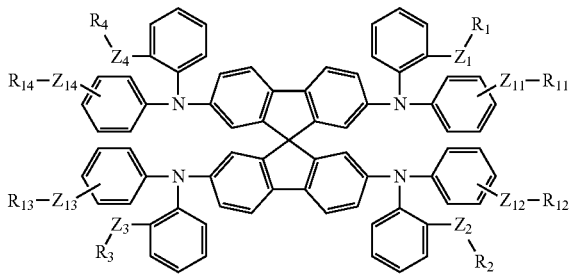

[In Chemical Formula 1, $Z_1$ to $Z_4$ and $Z_{11}$ to $Z_{14}$ are each independently O, S, or Se; and $R_1$ to $R_4$ and $R_{11}$ to $R_{14}$ are each independently (C1-C7) alkyl.]

In Chemical Formula 1 according to an exemplary embodiment of the present invention, $Z_1$ to $Z_4$ and $Z_{11}$ to $Z_{14}$ may be each independently O or S; and $R_1$ to $R_4$ and $R_{11}$ to $R_{14}$ may be each independently (C1-C3)alkyl.

Preferably, in Chemical Formula 1, $Z_1$ to $Z_4$ may be O; and $R_1$ to $R_4$ may be each independently (C1-C3)alkyl.

More preferably, the hole-transporting compound represented by Chemical Formula 1 may be represented by the following Chemical Formula 1-1.

[Chemical Formula 1-1]

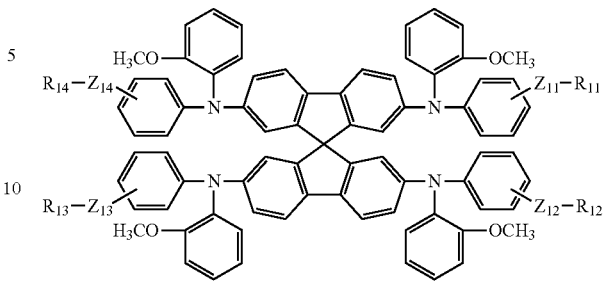

[In Chemical Formula 1-1, $Z_{11}$ to $Z_{14}$ are each independently O, S, or Se; and $R_{11}$ to $R_{14}$ are each independently (C$_1$-C7)alkyl.]

In another general aspect, a solar cell includes a hole transporting layer containing a hole-transporting compound for an inorganic/organic hybrid perovskite solar cell, represented by the following Chemical Formula 1.

[Chemical Formula 1]

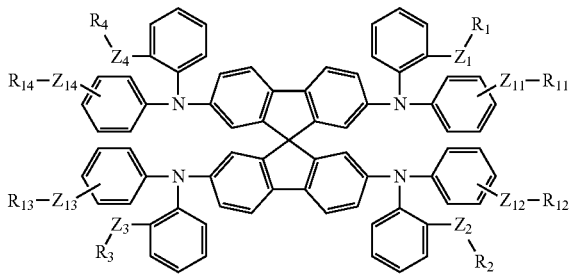

[In Chemical Formula 1, $Z_1$ to $Z_4$ and $Z_{11}$ to $Z_{14}$ are each independently O, S, or Se; and $R_1$ to $R_4$ and $R_{11}$ to $R_{14}$ are each independently (C1-C7) alkyl.]

The hole transporting layer of the solar cell may further contain a phthalocyanine derivative.

The phthalocyanine derivative may be represented by the following Chemical Formula 8.

[Chemical Formula 8]

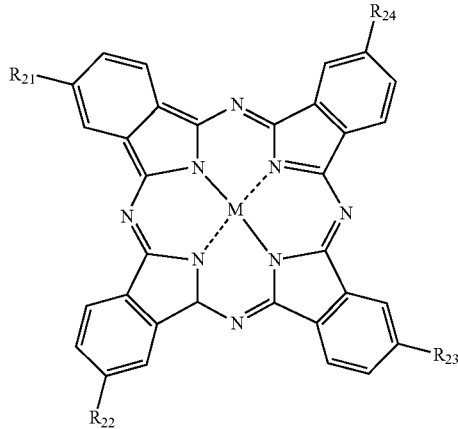

[In Chemical Formula 8,

M is copper (Cu), zinc (Zn), cobalt (Co), lead (Pb), silver (Ag), magnesium (Mg), iron (Fe), titanyl, or vanadyl; and $R_{21}$ to $R_{24}$ are each independently hydrogen, (C1-C7)alkyl, (C1-C7)alkoxy, or sulfonic acid group ($-SO_3H$).]

In the case of the phthalocyanine derivative according to an exemplary embodiment of the present invention, when the $R_{21}$ to $R_{24}$ are each independently (C1-C7)alkyl, a solubility for a solvent is improved, such that it is possible to perform a solution process as well as a evaporation deposition process on the phthalocyanine derivative, and properties of the hole transporting layer may be further improved.

The phthalocyanine derivative according to an exemplary embodiment of the present invention may be contained at a content of 0.1 to 15 parts by weight based on 100 parts by weight of the hole-transporting compound for an inorganic/organic hybrid perovskite solar cell.

The solar cell may be a solar cell including: a first electrode; a composite layer positioned on the first electrode and impregnated with a light harvester; a overlayer of light harvester positioned on the composite layer and made of the light harvester; the hole transporting layer positioned on the overlayer of light harvester; and a second electrode positioned on the hole transporting layer.

BRIEF DESCRIPTION OF THE DRAWINGS

FIG. 1 is a scanning electron microscope (SEM) photograph of a cross section of a solar cell manufactured according to Example 2 of the present invention, and it may be appreciated that a hole-transporting material synthesized in the present invention is uniformly applied at an upper portion of the solar cell.

DETAILED DESCRIPTION OF EMBODIMENTS

Hereinafter, a hole-transporting compound for an inorganic/organic hybrid perovskite solar cell will be described in detail. Here, technical terms and scientific terms used in the present specification have a general meaning understood by those skilled in the art to which the present invention pertains unless otherwise defined, and a description for the known function and configuration obscuring the present invention will be omitted in the following description and the accompanying drawings.

The present invention provides a hole-transporting compound for an inorganic/organic hybrid perovskite solar cell represented by the following Chemical Formula 1.

[Chemical Formula 1]

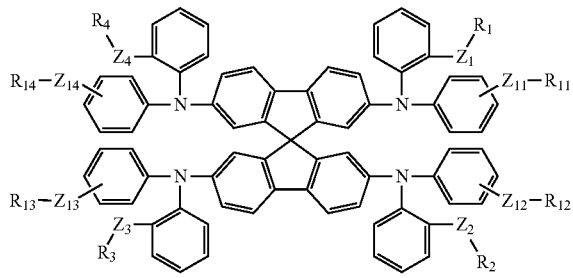

[In Chemical Formula 1, $Z_1$ to $Z_4$ and $Z_{11}$ to $Z_{14}$ are each independently O, S, or Se; and $R_1$ to $R_4$ and $R_{11}$ to $R_{14}$ are each independently (C1-C7)alkyl.]

The hole-transporting compound for an inorganic/organic hybrid perovskite solar cell represented by the following Chemical Formula 1 according to the present invention has significantly higher power generation efficiency than that of the existing spiro-OMeTAD by changing positions of four methoxy groups at specific positions among eight p-methoxy substituents, which are substituents of N,N-di-p-methoxyphenylamine in a spiro-OMeTAD compound, or positions and the kinds of substituents, unlike the existing spiro-OMeTAD.

In more detail, the spiro-OMeTAD, which is an existing hole-transporting compound, has a structure represented by the following Chemical Formula.

[Spiro-OMeTAD]

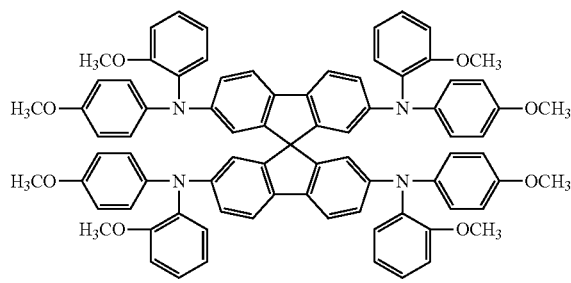 [SMILES: COc1ccc(N(c2ccc3c(c2)C2(c4cc(N(c5ccc(OC)cc5)c5ccccc5OC)ccc4-3)c3cc(N(c4ccc(OC)cc4)c4ccccc4OC)ccc3-c3ccc(N(c4ccc(OC)cc4)c4ccccc4OC)cc32)c2ccccc2OC)cc1]

As illustrated in the Chemical Formula, the spiro-OMeTAD has eight methoxy groups, and the present inventors found that when positions of four methoxy groups at specific positions among eight methoxy groups as described above, or positions and the kinds of substituents were changed and used as a hole-transporting compound of an inorganic/organic hybrid perovskite solar cell, power generation efficiency of the inorganic/organic perovskite solar cell was significantly improved, thereby completing the present invention.

In addition, since the hole-transporting compound for an inorganic/organic hybrid perovskite solar cell according to the present invention is a single molecule, the hole-transporting compound may be easily synthesized and easily separated, such that the compound having high purity may be obtained, which is significantly advantageous in view of commercial application.

In Chemical Formula 1 according to an exemplary embodiment of the present invention, $Z_1$ to $Z_4$ and $Z_{11}$ to $Z_{14}$ may be each independently O or S; and $R_1$ to $R_4$ and $R_{11}$ to $R_{14}$ may be each independently (C1-C3)alkyl.

Preferably, in Chemical Formula 1, $Z_1$ to $Z_4$ may be O; and $R_1$ to $R_4$ may be each independently (C1-C3)alkyl.

Preferably, the hole transporting compound represented by Chemical Formula 1 may be represented by the following Chemical Formula 1-1.

[Chemical Formula 1-1]

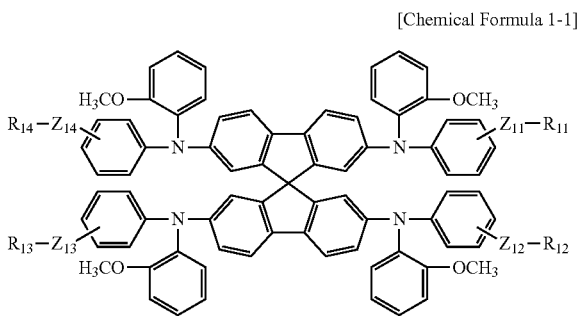

[In Chemical Formula 1-1, $Z_{11}$ to $Z_{14}$ are each independently O, S, or Se; and $R_{11}$ to $R_{14}$ are each independently (C$_1$-C7)alkyl.]

In the Chemical Formula 1 according to an exemplary embodiment of the present invention, in view of power generation efficiency, preferably, $Z_1$ to $Z_4$ may be O; and $R_1$ to $R_4$ may be each independently (C1-C3)alkyl, more specifically, $R_1$ to $R_4$ may be methyl or ethyl. More preferably, $Z_1$ to $Z_4$ may be O; and $R_1$ to $R_4$ may be all methyl.

The hole-transporting compound represented by Chemical Formula 1 according to the present invention may be prepared by the following Reaction Formula.

[Reaction Formula 1]

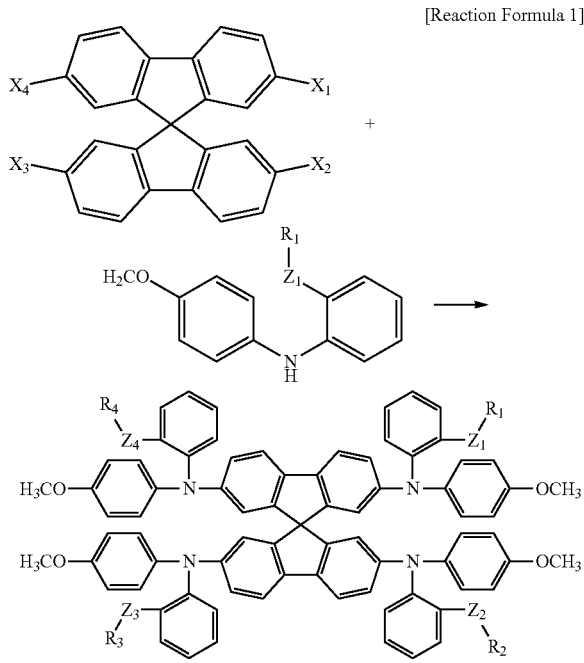

[In Reaction Formula 1, $Z_1$ to $Z_4$ and $R_1$ to $R_4$ have the same definitions as in Chemical Formula 1, and $X_1$ to $X_4$ are each independently halogen.]

Reaction Formula 1 is a reaction formula corresponding to the case in which $R_1$ to $R_4$ are the same as each other, but even in the case in which $R_1$ to $R_4$ are different from each other, the hole-transporting compound may be prepared by a synthesis method known to those skilled in the art.

The terms [alkyl], [alkoxy], and other substituents including a [alkyl] part disclosed in the present specification include both of the straight chain type and the branched chain type. In addition, the term [aryl] disclosed in the present specification, which is an organic radical derived from aromatic hydrocarbon by removing one hydrogen atom therefrom, may include a single ring or a fused ring containing, properly 4 to 7 ring atoms, and preferably, 5 or 6 ring atoms in each ring, and include rings in which two or more aryls are combined through single bond(s). A specific example of aryl may include phenyl, naphthyl, biphenyl, anthryl, indenyl, fluorenyl, and the like, but is not limited thereto.

The term [cycloalkyl] individually described herein or described as a part of another group in the present specification means a completely saturated or partially unsaturated hydrocarbon ring containing 3 to 9 carbon atoms and includes aryl or heteroaryl fused cycloalkyl.

The perovskite solar cell using the hole-transporting compound represented by Chemical Formula 1 according to the present invention, which is a general perovskite solar cell appreciated by those in skilled art, is not particularly limited, but may be a solar cell using a light harvester containing one or two or more materials selected from inorganic-organic hybrid perovskite compounds, CdS, CdSe, CdTe, PbS, PbSe, PbTe, Bi$_2$S$_3$, Bi$_2$Se$_3$, InP, InAs, InGaAs, ZnSe, ZnTe, GaN, GaP, GaAs, GaSb, InSb, Si, Ge, AlAs, AlSb, InCuS$_2$, In(CuGa)Se$_2$, Sb$_2$S$_3$, Sb$_2$Se$_3$, Sb$_2$Te$_3$, SnS$_x$(1≤x≤2), NiS, CoS, FeS$_x$(1≤x≤2), In$_2$S$_3$, MoS, MoSe, Cu$_2$S, HgTe, and MgSe.

Preferably, the light harvester of the inorganic/organic hybrid perovskite solar cell according to the present invention may be one or two or more materials selected from inorganic/organic hybrid perovskite compounds satisfying the following Chemical Formula 2 or 3.

AMX$_3$ (Chemical Formula 2)

(In Chemical Formula 2, A is a monovalent organic ammonium ion or Cs$^+$, M is a divalent metal ion, and X is a halogen ion.)

A$_2$MX$_4$ (Chemical Formula 3)

(In Chemical Formula 3, A is a monovalent organic ammonium ion or Cs$^+$, M is a divalent metal ion, and X is a halogen ion.)

In this case, M may be positioned at the center of a unit cell in a perovskite structure, X may be positioned at the center of each side of the unit cell to form an octahedron structure based on M, and A may be positioned at each corner of the unit cell.

In detail, the light harvester may be each independently one or two or more selected from compounds satisfying the following Chemical Formulas 4 to 7.

(R$_1$—NH$^{3+}$)MX$_3$ (Chemical Formula 4)

In Chemical Formula 4, R$_1$ is (C1-C24)alkyl, (C3-C20)cycloalkyl, or (C6-C20)aryl, M is one or two or more metal ions selected from Cu$^{2+}$, Ni$^{2+}$, Co$^{2+}$, Fe$^{2+}$, Mn$^{2+}$, Cr$^{2+}$, Pd$^{2+}$, Cd$^{2+}$, Ge$^{2+}$, Sn$^{2+}$, Pb$^{2+}$, and Yb$^{2+}$, and X is one or two or more halogen ions selected from Cl$^-$, Br$^-$, and I$^-$.

(R$_1$—NH$_3^+$)$_2$MX$_4$ (Chemical Formula 5)

In Chemical Formula 5, R$_1$ is (C1-C24)alkyl, (C3-C20)cycloalkyl, or (C6-C20)aryl, M is one or two or more metal ions selected from Cu$^{2+}$, Ni$^{2+}$, Co$^{2+}$, Fe$^{2+}$, Mn$^{2+}$, Cr$^{2+}$, Pd$^{2+}$, Cd$^{2+}$, Ge$^{2+}$, Sn$^{2+}$, Pb$^{2+}$, and Yb$^{2+}$, and X is one or two or more halogen ions selected from Cl$^-$, Br$^-$, and I$^-$.

(R$_2$—C$_3$H$_3$N$^{2+}$—R$_3$)MX$_3$ (Chemical Formula 6)

In Chemical Formula 6, R$_2$ is (C1-C24)alkyl, (C3-C20)cycloalkyl, or (C6-C20)aryl, R$_3$ is hydrogen or (C1-C24)alkyl, M is one or two or more metal ions selected from $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, and $Yb^{2+}$, and X is one or two or more halogen ions selected from $Cl^-$, $Br^-$, and $I^-$.

$$(R_2\text{—}C_3H_3N^{2+}\text{—}R_3)_2MX_4 \quad \text{(Chemical Formula 7)}$$

In Chemical Formula 7, $R_2$ is (C1-C24)alkyl, (C3-C20)cycloalkyl, or (C6-C20)aryl, $R_3$ is hydrogen or (C1-C24)alkyl, M is one or two or more metal ions selected from $Cu^{2+}$, $Ni^{2+}$, $Co^{2+}$, $Mn^{2+}$, $Cr^{2+}$, $Pd^{2+}$, $Cd^{2+}$, $Ge^{2+}$, $Sn^{2+}$, $Pb^{2+}$, and $Yb^{2+}$, and X is one or two or more halogen ions selected from $Cl^-$, $Br^-$, and $I^-$.

As an example, a compound having a perovskite structure may be $AMX^a{}_xX^b{}_y$ (x is real number satisfying $0 \le x \le 3$, y is real number satisfying $0 \le y \le 3$, x+y=3, and $X^a$ and $X^b$ are halogen ions different from each other) or $A_2MX^a{}_xX^b{}_y$ (x is real number satisfying $0 \le x \le 4$, y is real number satisfying $0 \le y \le 4$, x+y=4, and $X^a$ and $X^b$ are halogen ions different from each other).

As an example, in Chemical Formula 4 or 5, $R_1$ may be (C1-C24)alkyl, preferably (C1-C7)alkyl, and more preferably methyl. As a specific example, the compound having the perovskite structure may be one or two or more selected from $CH_3NH_3PbI_xCl_y$ (x is real number satisfying $0 \le x \le 3$, y is real number satisfying $0 \le u \le 3$, and x+y=3), $CH_3NH_3PbI_xBr_y$ (x is real number satisfying $0 \le x \le 3$, y is real number satisfying $0 \le y \le 3$, and x+y=3), $CH_3NH_3PbCl_xBr_y$ (x is real number satisfying $0 \le x \le 3$, y is real number satisfying $0 \le y \le 3$, and x+y=3), and $CH_3NH_3PbI_xF_y$ (x is real number satisfying $0 \le x \le 3$, y is real number satisfying $0 \le y \le 3$, and x+y=3). In addition, the compound having the perovskite structure may be one or two or more selected from $(CH_3NH_3)_2PbI_xCl_y$ (x is real number satisfying $0 \le x \le 4$, y is real number satisfying $0 \le y \le 4$, and x+y=4), $CH_3NH_3PbI_xBr_y$ (x is real number satisfying $0 \le x \le 4$, y is real number satisfying $0 \le y \le 4$, and x+y=4), $CH_3NH_3PbCl_xBr_y$ (x is real number satisfying $0 \le x \le 4$, y is real number satisfying $0 \le y \le 4$, and x+y=4), and $CH_3NH_3PbI_xF_y$ (x is real number satisfying $0 \le x \le 4$, y is real number satisfying $0 \le y \le 4$, and x+y=4).

As an example, in Chemical Formula 6 or 7, $R_2$ may be (C1-C24)alkyl, and $R_3$ may be hydrogen or (C1-C24)alkyl. Preferably, $R_2$ may be (C1-C7)alkyl, $R_3$ may be hydrogen or (C1-C7)alkyl. More preferably, $R_2$ may be methyl, and $R_3$ may be hydrogen.

The inorganic/organic hybrid perovskite solar cell according to the present invention includes: a first electrode; a composite layer positioned on the first electrode and impregnated with a light harvester; a overlayer of light harvester positioned on the composite layer and made of the light harvester; a hole transporting layer positioned on the overlayer of light harvester; and a second electrode positioned on the hole transporting layer, wherein the hole transporting layer contains the hole-transporting compound for an inorganic/organic hybrid perovskite solar cell according to the present invention.

In the case of applying the hole-transporting compound for an inorganic/organic hybrid perovskite based solar cell represented by Chemical Formula 1 according to the present invention to the inorganic/organic hybrid perovskite solar cell having a structural feature that the solar cell includes: the first electrode; the composite layer positioned on the first electrode and impregnated with the light harvester; the overlayer of light harvester positioned on the composite layer and made of the light harvester; the hole transporting layer positioned on the overlayer of light harvester; and the second electrode positioned on the hole transporting layer, the solar cell has higher power generation efficiency.

In the inorganic/organic hybrid perovskite solar cell having the above-mentioned structural feature, due to a double-layered structure of a light harvester layer including the composite layer and the overlayer of light harvester, the composite layer having a structure in which an electron carrier and the light harvester are impregnated thereinto, and the overlayer of light harvester being formed on the composite layer, a structure in which the electron carrier and the hole-transporting compound are organically bonded to each other, and a high LUMO level, released electrons may be efficiently blocked, such that the inorganic/organic hybrid perovskite solar cell have high power generation efficiency. Further, a synergy effect on power generation efficiency is implemented by applying the compound of Chemical Formula 1, which is the hole-transporting compound for a inorganic/organic hybrid perovskite solar cell according to the present invention, to the structure of the inorganic/organic hybrid perovskite solar cell, such that the inorganic/organic hybrid perovskite solar cell may have higher power generation efficiency.

That is, the hole-transporting compound represented by Chemical Formula 1 according to the present invention may also have a structure in which the light harvester fill in a porous electron carrier and the overlayer of light harvester made of the light harvester is positioned on a porous electron carrier rather than a structure in which the light harvester is dispersed and impregnated in the porous electron carrier, and in the case in which the hole-transporting compound is applied to the hole transporting layer of the inorganic/organic hybrid perovskite solar cell having a structural feature that which the light harvester covers an upper portion of the porous electron carrier, the solar cell has higher power generation efficiency.

The hole-transporting compound, the light harvester, the electron carrier, the hole transporting layer, and the like, as used herein correspond to definitions that may be clearly understood by those skilled in the art.

The hole transporting layer of the solar cell according to the exemplary embodiment of the present invention may contain the hole-transporting compound for an inorganic/organic hybrid perovskite solar cell and a phthalocyanine derivative.

The phthalocyanine derivative is doped on the hole transporting layer together with the hole-transporting compound for an inorganic/organic hybrid perovskite solar cell, thereby making it possible to implement higher efficiency, wherein the phthalocyanine derivative may be a compound represented by the following Chemical Formula 8.

[Chemical Formula 8]

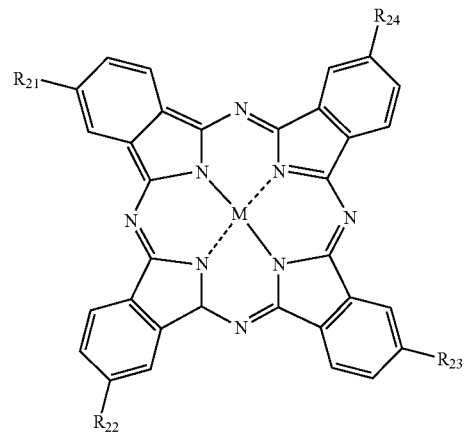

[In Chemical Formula 8,
M is copper (Cu), zinc (Zn), cobalt (Co), lead (Pb), silver (Ag), magnesium (Mg), iron (Fe), titanyl, or vanadyl; and
$R_{21}$ to $R_{24}$ are each independently hydrogen, (C1-C7)alkyl, (C1-C7)alkoxy, or sulfonic acid group (—$SO_3H$).]

More specifically, in the case in which M of the phthalocyanine derivative represented by Chemical Formula 8 is copper (Cu), zinc (Zn), or cobalt (Co), a leakage current of the solar cell may be completely blocked, and an electron blocking property may be improved by trapping the unwanted electrons in CuPC-doped hole transporting layer, such that a solar cell having higher efficiency may be provided.

The phthalocyanine derivative represented by Chemical Formula 8 according to an exemplary embodiment of the present invention may be added at a content of 0.1 to 15 parts by weight, preferably 1 to 15 parts by weight, and more preferably 2 to 10 parts by weight based on 100 parts by weight of the hole-transporting compound for an inorganic/organic hybrid perovskite solar cell, which is preferable in view of further improving the electron blocking property.

Further, the present invention provides an inorganic/organic hybrid perovskite solar cell containing the hole-transporting compound for an inorganic/organic hybrid perovskite solar cell represented by Chemical Formula 1 according to the present invention, and a solar cell module including the solar cell as described above.

Hereinafter, specific Examples of the present invention will be described in detail by way of example, but the present invention is not limited thereto.

Example 1

Preparation of 2,4'-dimethoxydiphenylamine

Anisidine (2.00 g, 16.2 mmol), 4-bromoaniline (3.34 g, 17.9 mmol), sodium tert-butoxide (2.34 g, 24.4 mmol), tris(dibenzylideneacetone)dipalladium(0) (0.149 g, 0.162 mmol), and tri-tertbutylphosphine (0.053 g, 0.26 mmol) were put into a 100 mL 2-neck flask under nitrogen atmosphere, and 23 mL of anhydrous toluene was added thereto and stirred at 110° C. for 12 hours. When a reaction was completed, a reaction mixture was extracted with ethyl acetate, washed with salt water, and dried over MgSO4 to remove a solvent, followed by separation and purification using column chromatography (ethyl acetate/hexane=1/10), thereby obtaining the title compound (54%, 2.01 g) as a sticky solid.
$^1$H-NMR (CDCl$_3$, 300 MHz) δ=7.11 (d, 2H), 7.03 (dd, 1H), 6.75-6.90 (m, 5H), 5.98 (br s, 1H), 3.90 (s, 3H), 3.80 (s, 1H).

Preparation of N$^2$,N$^{2'}$,N$^7$,N$^{7'}$-tetrakis(2-methoxyphenyl)-N$^2$,N$^{2'}$,N$^7$,N$^{7'}$-tetrakis (4-methoxyphenyl)-9,9'spirobi[fluorene]-2,2',7,7'tetraamine (hereinafter, referred to as po)

2,4'-Dimethoxydiphenylamine (2.00 g, 8.72 mmol), 2,2',7,7'-tetrabromo-9,9'spirobi[9H-fluorene] (1.23 g, 1.94 mmol), sodium tertbutoxide (1.12 g, 11.6 mmol), tris(dibenzylideneacetone)dipalladium(0) (0.071 g, 0.078 mmol), and tri-tert-butylphosphine (0.025 g, 0.12 mmol) were put into a 50 mL 2-neck flask under nitrogen atmosphere, and 15 mL of anhydrous toluene was added thereto and stirred at 110° C. for 12 hours. A reaction mixture was cooled to room temperature, extracted with ethyl acetate, washed with salt water, and dried over MgSO$_4$ to remove a solvent, followed by separation and purification using column chromatography (ethyl acetate/hexane=1/2), thereby obtaining the title compound (40%, 0.95 g) as a beige solid.
$^1$H-NMR (CDCl$_3$, 500 MHz) δ=7.32 (d, 4H), 7.08 (7, 4H), 6.96 (d, 4H), 6.86 (q, 16H), 6.72 (d, 12H), 6.40 (s, 4H), 3.75 (s, 12H), 3.47 (s, 12H).
$^{13}$C-NMR (CDCl$_3$, 125 MHz) δ=154.95, 154.55, 149.83, 146.84, 141.29, 136.08, 135.09, 128.48, 125.39, 125.59, 121.24, 120.70, 119.19, 116.52, 113.96, 113.09, 65.65, 55.70, 55.39.
m/z 1124 (M+).

Comparative Example 1

Preparation of N$^2$,N$^2$,N$^{2'}$,N$^{2'}$,N$^7$,N$^7$,N$^{7'}$,N$^{7'}$-octakis (4-methoxyphenyl)-9,9'spirobi[fluorene]-2,2',7,7'-tetraamine(spiro-OMeDTAD, hereinafter, referred to as pp)

4,4'-Dimethoxydiphenylamine (2.00 g, 8.72 mmol), 2,2',7,7'-tetrabromo-9,9'spirobi[9H-fluorene] (1.23 g, 1.94 mmol), sodium tertbutoxide (1.12 g, 11.6 mmol), tris(dibenzylideneacetone)dipalladium(0) (0.071 g, 0.078 mmol), and tri-tert-butylphosphine (0.025 g, 0.12 mmol) were put into a 50 mL 2-neck flask under nitrogen atmosphere, and 15 mL of anhydrous toluene was added thereto and stirred at 110° C. for 12 hours. A reaction mixture was cooled to room temperature, extracted with ethyl acetate, washed with salt water, and dried over MgSO4 to remove a solvent, followed by separation and purification using column chromatography (ethyl acetate/hexane=1/2), thereby obtaining the title compound (45%, 1.07 g) as a beige solid.
$^1$H-NMR (CDCl$_3$, 500 MHz) δ=7.36 (d, 4H), 6.91 (d, 16H), 6.80 (br d, 4H), 6.76 (d, 16H), 6.56 (s, 4H), 3.77 (s, 24H).
$^{13}$C-NMR (CDCl$_3$, 125 MHz) δ=154.95, 149.93, 147.11, 141.45, 135.46, 124.96, 122.67, 119.72, 118.03, 114.31, 65.45, 55.42.
m/z 1124 (M+).

Comparative Example 2

Preparation of 3,4-dimethoxydiphenyleneamine m-Anisidine (2.00 g, 16.2 mmol), 4-bromoaniline (3.34 g, 17.9 mmol), sodium tert-butoxide (2.34 g, 24.4 mmol), tris(dibenzylideneacetone)dipalladium(0) (0.149 g, 0.162 mmol), and tri-tertbutylphosphine (0.053 g, 0.26 mmol)) were put into a 100 mL 2-neck flask under nitrogen atmosphere, and 23 mL of anhydrous toluene was added thereto and stirred at 110° C. for 12 hours. When a reaction was completed, a reaction mixture was extracted with ethyl acetate, washed with salt water, and dried over MgSO$_4$ to remove a solvent, followed by separation and purification using column chromatography (ethyl acetate/hexane=1/10), thereby obtaining the title compound (54%, 2.01 g) as a sticky solid.
$^1$H-NMR (CDCl$_3$, 300 MHz) δ=7.05-7.15 (m, 3H), 6.87 (d, 2H), 6.35-6.53 (m, 3H), 5.50 (br s, 1H), 3.80 (s, 3H), 3.76 (s, 3H).

Preparation of N$^2$,N$^{2'}$,N$^7$,N$^{7'}$-tetrakis(3-methoxyphenyl)-N$^2$,N$^{2'}$,N$^7$,N$^{7'}$-tetrakis(4-methoxyphenyl)-9,9'spirobi[fluorene]-2,2',7,7'tetraamine (hereinafter, referred to as pm)

2,4'-Dimethoxydiphenylamine (2.00 g, 8.72 mmol), 2,2',7,7'-tetrabromo-9,9'spirobi[9H-fluorene] (1.23 g, 1.94 mmol), sodium tertbutoxide (1.12 g, 11.6 mmol), tris(dibenzylideneacetone)dipalladium(0) (0.071 g, 0.078 mmol), and tri-tert-butylphosphine (0.025 g, 0.12 mmol) were put into a 50 mL 2-neck flask under nitrogen atmosphere, and 15 mL of anhydrous toluene was added thereto and stirred at 110° C. for 12 hours. A reaction mixture was cooled to room temperature, extracted with ethyl acetate, washed with salt water, and dried over $MgSO_4$ to remove a solvent, followed by separation and purification using column chromatography (ethyl acetate/hexane=1/2), thereby obtaining the title compound (40%, 0.95 g) as a beige solid.

$^1$H-NMR ($CDCl_3$, 500 MHz) δ=7.42 (d, 4H), 7.05 (t, 4H), 6.97 (d, 8H), 6.88 (d, 4H), 6.81 (d, 8H), 6.65 (d, 4H), 6.40-6.51 (m, 12H).

$^{13}$C-NMR ($CDCl_3$, 125 MHz) δ=160.17, 155.87, 129.80, 149.37, 146.583, 140.45, 136.19, 129.44, 126.80, 123.98, 120.08, 119.18, 114.52, 114.01, 107.35, 106.44, 65.51, 55.40, 55.11.

m/z 1124 (M+).

Example 2

Manufacturing of Porous $TiO_2$ Thin Film Substrate

After a glass substrate on which fluorine doped tin oxide (FTO; F-doped $SnO_2$, 8 ohms/$cm^2$, Pilkington, hereinafter, FTO substrate (first electrode)) was coated was cut at a size of 25×25 mm, end portions thereof were etched to partially remove FTO.

A dense $TiO_2$ film having a thickness of 50 nm was manufactured on the cut and partially etched FTO substrate by a spray pyrolysis method (SPM) as a metal oxide thin film. The SPM was performed using a titanium acetylacetonate (TAA):EtOH(1:9 v/v %) solution, and the thickness was adjusted by repeating a process of spraying the solution onto the FTO substrate positioned on a hot plate maintained at 450° C. for 3 seconds and stopping for 10 seconds.

5 ml of an ethyl cellulose solution in which 10 wt % of ethyl cellulose was dissolved in ethyl alcohol was added to $TiO_2$ powder having an average particle size (diameter) of 50 nm (prepared by hydrothermal treatment of an aqueous solution in which a titanium peroxo complex (1 wt % based on $TiO_2$) was dissolved at 250° C. for 12 hours) per 1 g of $TiO_2$ powder, and 5 g of terpinol was added thereto per 1 g of $TiO_2$ powder and then mixed, followed by removing ethyl alcohol by a vacuum distillation method, thereby preparing a $TiO_2$ paste.

Ethanol was added to the prepared $TiO_2$ paste, thereby preparing $TiO_2$ slurry for spin coating. The prepared $TiO_2$ slurry for spin coating was coated onto the $TiO_2$ thin film on the FTO substrate by a spin coating method and heat-treated at 500° C. for 60 minutes. Then, after the heat-treated substrate was immersed in 30 mM $TiCl_4$ aqueous solution at 60° C. and left for about 30 minutes, the substrate was washed and dried using deionized water and ethanol, followed by heat-treatment at 500° C. for 30 minutes, thereby manufacturing a porous $TiO_2$ thin film (porous electron carrier).

Preparation of Light Harvester Solution 30 mL of hydrochloric acid (57% in water, Aldrich) and 27.86 mL of methylamine (40% in methanol, Junsei Chemical Co., Ltd.) were reacted with each other in a 250 mL 2-neck round flask at 0° C. for 2 hours. A precipitate obtained by distilling a reaction mixture at 50° C. for 1 hour under reduced pressure was dissolved in ethanol, re-crystallized using ethylether, and dried at 60° C. for 24 hours, thereby preparing $CH_3NH_3I$.

The obtained $CH_3NH_3I$ was dissolved in a mixed solution of γ-butyrolactone and dimethylsulfoxide (7:3), $PbI_2$ (Aldrich) was added thereto and dissolved at 60° C. for 12 hours, thereby preparing 1.2M $CH_3NH_3PbI_3$ solution (40 wt %).

Manufacturing of Perovskite Light Harvester

The prepared light harvester solution ($CH_3NH_3PbI_3$ solution) was coated onto the porous $TiO_2$ thin film substrate (mp-$TiO_2$/bl-$TiO_2$/FTO) manufactured as described above at 1000 rpm for 90 seconds, and coated again at 5000 rpm for 30 seconds, followed by drying at 1000 for 10 minutes, thereby manufacturing the light harvester. Here, 1 mL of toluene was added dropwise onto the substrate in a second spin coating step.

Preparation of HTM Solution for Forming Hole Transporting Layer

In order to form a hole transporting layer, a HTM solution having a concentration of 10 mM was prepared by dissolving $N^2,N^{2'},N^7,N^{7'}$-tetrakis(2-methoxyphenyl)-$N^2,N^{2'},N^7,N^{7'}$-tetrakis(4-methoxyphenyl)-9,9'spirobi[fluorene]-2,2',7,7'tetraamine (po), which was a hole conductor prepared in Example 1, in toluene, and 10 μL of Li-bis(trifluoromethanesulfonyl) imide (Li-TFSI)/acetonitrile (170 mg/1 ml) and 5 μL of 4-tert-butylpyridine (TBP) were added thereto as additives, thereby preparing the HTM solution.

Manufacturing of Inorganic/Organic Hybrid Perovskite Solar Cell

The prepared HTM solution was spin coated on a composite layer in which the manufactured overlayer of light harvester was formed on the manufactured porous electrode at 3000 rpm for 30 seconds, thereby forming a hole transporting layer.

Thereafter, Au was vacuum deposited on an upper portion of the hole transporting layer using high vacuum ($5 \times 10^{-6}$ torr or less) thermal evaporator, such that an Au electrode (second electrode) at a thickness of about 70 nm was formed, thereby manufacturing an Au/hole transporting layer/$CH_3NH_3PbI_3$/mp-$TiO_2$/bl-$TiO_2$/FTO solar cell.

An active area of the electrode as described above was 0.16 $cm^2$.

A SEM photograph of a cross section of the manufactured solar cell was illustrated in FIG. 1, and characteristics of the manufactured solar cell were illustrated in the following Table 1.

Comparative Example 3

A solar cell was manufactured in the same manner except for using pp (spiro-OMeTAD) instead of po as the HTM solution, and characteristics of the manufactured solar cell were illustrated in the following Table 1.

Comparative Example 4

A solar cell was manufactured in the same manner except for using pm instead of po as the HTM solution, and characteristics of the manufactured solar cell were illustrated in the following Table 1.

Comparative Example 5

A solar cell was manufactured in the same manner except for using commercially sold pp instead of po as the HTM solution, and characteristics of the manufactured solar cell were illustrated in the following Table 1.

TABLE 1

|  | HTMs (spiro-OMeTAD) | Jsc (mA/cm$^2$) | Voc (V) | FF | PCE (%) |
|---|---|---|---|---|---|
| Comparative Example 5 | Commercialized pp | 20.4 | 1.00 | 73.7 | 15.2 |
| Comparative Example 4 | pm | 21.1 | 1.01 | 65.2 | 13.9 |
| Example 2 | po | 21.2 | 1.02 | 77.6 | 16.7 |
| Comparative Example 3 | pp | 20.7 | 1.00 | 71.1 | 14.9 |

As illustrated in Table 1, the solar cell using the hole-transporting compound according to the present invention had significantly higher efficiency as compared to solar cells using the existing hole-transporting compounds.

Example 3

Manufacturing of Porous TiO$_2$ Thin Film Substrate

After a glass substrate on which fluorine doped tin oxide (FTO; F-doped SnO$_2$, 8 ohms/cm$^2$, Pilkington, hereinafter, FTO substrate (first electrode)) was coated was cut at a size of 25×25 mm, end portions thereof were etched to partially remove FTO.

A dense TiO$_2$ film having a thickness of 50 nm was manufactured on the cut and partially etched FTO substrate by a spray pyrolysis method (SPM) as a metal oxide thin film. The SPM was performed using a 20 mM titanium diisopropoxide bis(acetylacetonate) solution (Aldrich), and the thickness was adjusted by repeating a process of spraying the solution onto the FTO substrate positioned on a hot plate maintained at 450° C. for 3 seconds and stopping for 10 seconds.

5 ml of an ethyl cellulose solution in which 10 wt % of ethyl cellulose was dissolved in ethyl alcohol was added to TiO$_2$ powder having an average particle size of 50 nm (prepared by hydrothermal treatment of an aqueous solution in which a titanium peroxo complex (1 wt % based on TiO$_2$) was dissolved at 250° C. for 12 hours) per 1 g of TiO$_2$ powder and 5 g of terpinol was added thereto per 1 g of TiO$_2$ powder and then mixed, followed by removing ethyl alcohol by a vacuum distillation method, thereby preparing a TiO$_2$ paste.

2-methoxyethanol was added to the prepared TiO$_2$ paste, thereby preparing TiO$_2$ slurry for spin coating. The prepared TiO$_2$ slurry for spin coating was coated onto the TiO$_2$ thin film on the FTO substrate by a spin coating method and heat-treated at 500° C. for 60 minutes. Then, after the heat-treated substrate was immersed in 30 mM TiCl$_4$ aqueous solution at 60° C. and left for 30 minutes, the substrate was washed and dried using deionized water and ethanol, followed by heat-treatment at 500° C. for 30 minutes again, thereby manufacturing a porous TiO$_2$ thin film (porous electron carrier, thickness: 100 nm).

Preparation of Light Harvester Solution

NH$_2$CH=NH$_2$I (=FAI) and CH$_3$NH$_3$Br (=MABr) were mixed with PbI$_2$ and PbBr$_2$ dissolved in a mixed solution of DMF and DMSO (6:1, v/v) in a 250 mL 2-neck round flask, thereby preparing 1.05M (FAPbI$_3$)$_{0.85}$ (MAPbBr$_3$)$_{0.15}$ perovskite solution.

Manufacturing of Perovskite Light Harvester

The prepared light harvester solution ((FAPbI$_3$)$_{0.85}$ (MAPbBr$_3$)$_{0.15}$ perovskite solution) was coated onto the porous TiO$_2$ thin film substrate (mp-TiO$_2$/bl-TiO$_2$/FTO) manufactured as described above at 1000 rpm for 5 seconds, and coated again at 5000 rpm for 1 second, followed by drying at 100° C. for 10 minutes, thereby manufacturing the light harvester. Here, 1 mL of diethylether was added dropwise onto the substrate in a second spin coating step.

Preparation of HTM Solution for Forming Hole Transporting Layer

In order to form a hole transporting layer, a HTM solution having a concentration of 30 mg/ml was prepared by dissolving N$^2$,N$^{2'}$,N$^7$,N$^{7'}$-tetrakis(2-methoxyphenyl)-N$^2$,N$^{2'}$, N$^7$,N$^{7'}$-tetrakis(4-methoxyphenyl)-9,9'spirobi[fluorene]-2, 2',7,7'tetraamine (po), which was a hole conductor prepared in Example 1, in toluene, and 21.5 μL of Li-bis(trifluoromethanesulfonyl) imide (Li-TFSI)/acetonitrile (170 mg/1 ml), 21.5 μL of 4-tert-butylpyridine (TBP), and 19.8 μL of tris(2-(1H-pyrazol-1-yl)-4-tert-butylpyridine)-cobalt(III) tris(bis(trifluoromethylsulfonyl)imide:(FK209)/acetonitrile (150 mg/1 ml) were added thereto as additives, thereby preparing the HTM solution.

Manufacturing of Inorganic/Organic Hybrid Perovskite Solar Cell

The prepared HTM solution was spin coated on a composite layer in which the manufactured overlayer of light harvester was formed on the manufactured porous electrode at 3000 rpm for 30 seconds, thereby forming a hole transporting layer.

Thereafter, Au was vacuum deposited on an upper portion of the hole transporting layer using high vacuum (5×10$^{-6}$ torr or less) thermal evaporator, such that an Au electrode (second electrode) at a thickness of 70 nm was formed, thereby manufacturing a Au/hole transporting layer/ (FAPbI$_3$)$_{0.85}$ (MAPbBr$_3$)$_{0.15}$/mp-TiO$_2$/bl-TiO$_2$/FTO solar cell.

An active area of the electrode as described above was 0.16 cm$^2$.

The property of the manufactured solar cell was shown in the following Table 2.

Example 4

A solar cell was manufactured by the same method as in Example 3 except for further adding 0.61 mg of copper (II) 2,9,16,23-tetra-tert-butyl-29H, 31H-phthalocyanine(tert-butylCuPC, CuPC) as an additive at the time of preparing the HTM solution for forming the hole transporting layer, and the properties of the solar cell were shown in the following Table 2.

Example 5

A solar cell was manufactured by the same method as in Example 3 except for further adding 1.51 mg of copper (II) 2,9,16,23-tetra-tert-butyl-29H,31H-phthalocyanine(tert-butylCuPC, CuPC) as an additive at the time of preparing the HTM solution for forming the hole transporting layer, and the properties of the solar cell were shown in the following Table 2.

Example 6

A solar cell was manufactured by the same method as in Example 3 except for further adding 3.0 mg of copper (II) 2,9,16,23-tetra-tert-butyl-29H, 31H-phthalocyanine(tert-butylCuPC, CuPC) as the additive at the time of preparing the HTM solution for forming the hole transporting layer, and the properties of the solar cell were shown in the following Table 2.

Comparative Example 6

A solar cell was manufactured by the same method as in Example 3 except for further adding 6.01 mg of copper (II) 2,9,16,23-tetra-tert-butyl-29H, 31H-phthalocyanine(tert-butylCuPC, CuPC) as an additive at the time of preparing the HTM solution for forming the hole transporting layer, and the properties of the solar cell were shown in the following Table 2.

TABLE 2

|  | CuPC (based on 100 parts by weight of po) | $J_{sc}$ (mA/cm²) | $V_{oc}$ (V) | FF | PCE (%) | $R_{shunt}$ (KΩcm²) |
|---|---|---|---|---|---|---|
| Example 3 | — | 22.4 | 1.09 | 71.85 | 17.5 | 80.79 |
| Example 4 | 2.0 | 22.3 | 1.10 | 72.8 | 17.9 | 105.22 |
| Example 5 | 4.8 | 22.3 | 1.11 | 74.7 | 18.5 | 160.76 |
| Example 6 | 9.1 | 22.3 | 1.10 | 74.2 | 18.2 | 113.41 |
| Comparative Example 6 | 16.7 | 22.3 | 1.07 | 71.3 | 17.0 | 46.70 |

As shown in Table 2, it may be appreciated that shunt resistance ($R_{shunt}$) was improved by further adding CuPC, which is the compound represented by Chemical Formula 8 according to the present invention, to the hole transporting layer.

That is, the electron blocking property is further improved by trapping the unwanted electrons in CuPC-doped hole transporting layer, such that more excellent photovoltaic conversion efficiency may be implemented.

The hole-transporting compound for an inorganic/organic hybrid perovskite solar cell represented by Chemical Formula 1 according to the present invention has a high LUMO level as compared to the existing spiro-OMeTAD, thereby making it possible to significantly improve power generation efficiency.

In addition, since the hole-transporting compound for an inorganic/organic hybrid perovskite solar cell represented by Chemical Formula 1 according to the present invention is the single molecule, the hole-transporting compound may be manufactured and separated by a simple process unlike the existing polymer hole-transporting compound, which is significantly advantageous in view of commercial application.

In addition, the hole-transporting compound for an inorganic/organic hybrid perovskite solar cell represented by Chemical Formula 1 according to the present invention may be applied as the hole-transporting compound of the inorganic/organic hybrid perovskite solar cell that may be manufactured as an all-solid phase, and the inorganic/organic hybrid perovskite solar cell using the hole-transporting compound may have high power generation efficiency and excellent stability and be manufactured by a simple solution application method, such that the solar cell may be mass-produced at low cost in a short time, which is significantly useful for manufacturing a solar cell at low cost.

What is claimed is:

1. A hole-transporting compound for an inorganic/organic hybrid perovskite solar cell, the hole-transporting compound represented by Chemical Formula 1, Chemical Formula 1

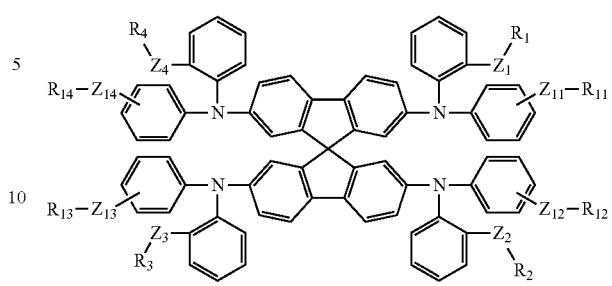

in Chemical Formula 1,
$Z_1$ to $Z_4$ and $Z_{11}$ to $Z_{14}$ are each independently O, S, or Se; and
$R_1$ to $R_4$ and $R_{11}$ to $R_{14}$ are each independently (C1-C7) alkyl.

2. The hole-transporting compound of claim 1, wherein $Z_1$ to $Z_4$ and $Z_{11}$ to $Z_{14}$ are each independently O or S; and
$R_1$ to $R_4$ and $R_{11}$ to $R_{14}$ are each independently (C1-C3) alkyl.

3. The hole-transporting compound of claim 2, wherein $Z_1$ to $Z_4$ are O; and
$R_1$ to $R_4$ are each independently (C1-C3)alkyl.

4. The hole-transporting compound of claim 1, wherein the hole-transporting compound of Chemical Formula 1 is represented by the following Chemical Formula 1-1, Chemical Formula 1-1

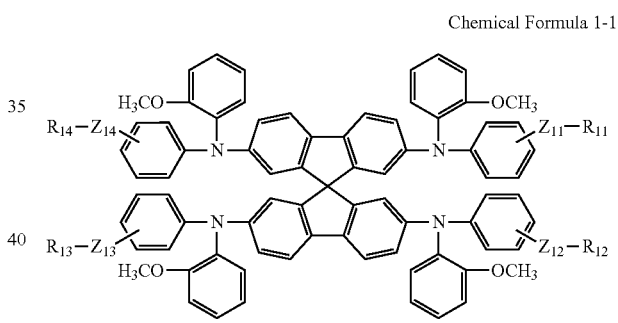

in Chemical Formula 1-1,
$Z_{11}$ to $Z_{14}$ are each independently O, S, or Se; and
$R_{11}$ to $R_{14}$ are each independently ($C_1$-C7)alkyl.

5. A solar cell comprising a hole transporting layer containing a hole-transporting compound for an inorganic/organic hybrid perovskite solar cell, represented by the following Chemical Formula 1, Chemical Formula 1

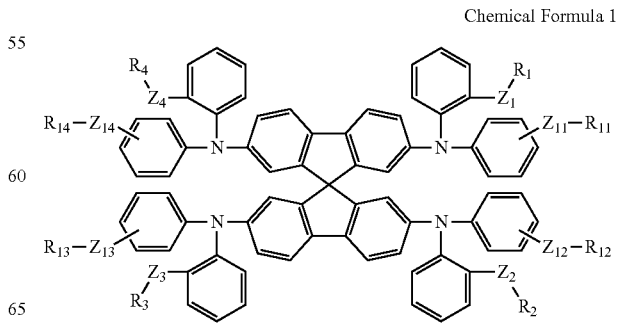

in Chemical Formula 1, $Z_1$ to $Z_4$ and $Z_{11}$ to $Z_{14}$ are each independently O, S, or Se; and $R_1$ to $R_4$ and $R_{11}$ to $R_{14}$ are each independently (C1-C7) alkyl.

6. The solar cell of claim 5, wherein the hole transporting layer further contains a phthalocyanine derivative.

7. The solar cell of claim 6, wherein the phthalocyanine derivative is represented by the following Chemical Formula 8, Chemical Formula 8

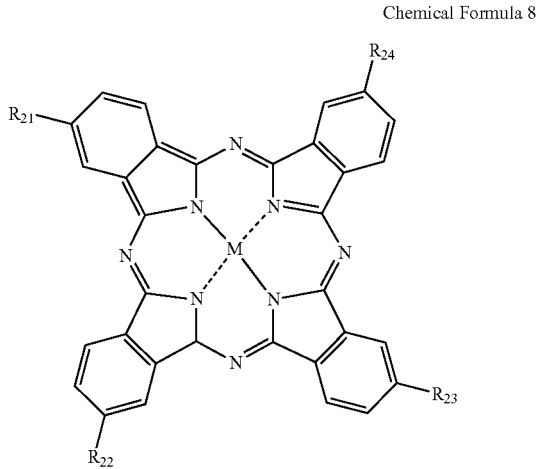

in Chemical Formula 8,

M is copper (Cu), zinc (Zn), cobalt (Co), lead (Pb), silver (Ag), magnesium (Mg), iron (Fe), titanyl, or vanadyl; and $R_{21}$ to $R_{24}$ are each independently hydrogen, (C1-C7) alkyl, (C1-C7)alkoxy, or sulfonic acid group ($-SO_3H$).

8. The solar cell of claim 7, wherein the phthalocyanine derivative is contained at a content of 0.1 to 15 parts by weight based on 100 parts by weight of the hole-transporting compound for an inorganic/organic hybrid perovskite solar cell.

9. The solar cell of claim 5, wherein it includes: a first electrode; a composite layer positioned on the first electrode and impregnated with a light harvester; a overlayer of light harvester positioned on the composite layer and made of the light harvester; the hole transporting layer positioned on the overlayer of light harvester; and a second electrode positioned on the hole transporting layer.

* * * * *